(12) United States Patent
Sallee et al.

(10) Patent No.: US 10,758,144 B2
(45) Date of Patent: Sep. 1, 2020

(54) FLEXIBLE ELECTRODE FOR CARDIAC SENSING AND METHOD FOR MAKING

(71) Applicant: Boston Scientific Scimed Inc., Maple Grove, MN (US)

(72) Inventors: Gregory Sallee, Arden Hills, MN (US); Kenneth L. Gunter, Maple Grove, MN (US); Danielle Frankson, Dayton, MN (US); Patrick A. Merriam, St. Paul, MN (US); Edward J. Maierhofer, Brooklyn Park, MN (US); Matthew P. Jones, Shoreview, MN (US)

(73) Assignee: Boston Scientific Scimed Inc., Maple Grove, MN (US)

( * ) Notice: Subject to any disclaimer, the term of this patent is extended or adjusted under 35 U.S.C. 154(b) by 916 days.

(21) Appl. No.: 15/239,245

(22) Filed: Aug. 17, 2016

(65) Prior Publication Data

US 2017/0049349 A1     Feb. 23, 2017

Related U.S. Application Data

(60) Provisional application No. 62/207,814, filed on Aug. 20, 2015.

(51) Int. Cl.
  *C25D 11/26*     (2006.01)
  *A61B 5/042*     (2006.01)
  (Continued)

(52) U.S. Cl.
  CPC .......... *A61B 5/0422* (2013.01); *A61B 5/6858* (2013.01); *A61L 29/02* (2013.01);
  (Continued)

(58) Field of Classification Search
  None
  See application file for complete search history.

(56) References Cited

U.S. PATENT DOCUMENTS

| 4,573,481 A | 3/1986 | Bullara |
| 4,649,924 A | 3/1987 | Taccardi |

(Continued)

FOREIGN PATENT DOCUMENTS

| CA | 2719329 A1 | 10/2009 |
| CN | 203017083 U | 6/2013 |

(Continued)

OTHER PUBLICATIONS

Written Opinion of International Searching Authority issued in PCT/US2009/061277, dated Apr. 8, 2010, 10 pages.

(Continued)

*Primary Examiner* — Stefanie S Wittenberg
(74) *Attorney, Agent, or Firm* — Faegre Drinker Biddle & Reath LLP

(57) ABSTRACT

An electrode for cardiac signal sensing includes an intermediate layer, an iridium-containing layer, an iridium oxide layer, an insulating polymer layer, and a conductive layer formed on a flexible polymer substrate. The intermediate metal layer has a first portion and a second portion, and is formed on the conductive layer. The iridium-containing layer includes at least 50 wt. % iridium and has a first portion and a second portion, and is formed on the first portion of the intermediate metal layer. The iridium oxide layer is formed on the first portion of the iridium-containing layer. The insulating polymer layer is formed on the second portion of the intermediate metal layer and the second portion of the iridium-containing layer. The iridium-containing layer is not formed on the second portion of the intermediate metal layer; and the iridium oxide layer is not formed on the second portion of the iridium-containing layer.

9 Claims, 6 Drawing Sheets

(51) Int. Cl.
*A61B 5/00* (2006.01)
*A61L 29/02* (2006.01)
*B05D 1/00* (2006.01)
*B05D 3/06* (2006.01)
*C23C 14/04* (2006.01)
*C23C 14/16* (2006.01)
*C23C 14/58* (2006.01)

(52) U.S. Cl.
CPC ............... *B05D 1/60* (2013.01); *B05D 3/06* (2013.01); *C23C 14/042* (2013.01); *C23C 14/165* (2013.01); *C23C 14/5813* (2013.01); *C25D 11/26* (2013.01); *A61B 2562/125* (2013.01)

(56) References Cited

U.S. PATENT DOCUMENTS

| | | | |
|---|---|---|---|
| 4,674,518 A | 6/1987 | Salo | |
| 4,732,662 A * | 3/1988 | Holscher | A61B 5/14539 204/291 |
| 4,762,136 A | 8/1988 | Baker et al. | |
| 4,840,182 A | 6/1989 | Carlson | |
| 4,920,490 A | 4/1990 | Isaacson | |
| 5,156,151 A | 10/1992 | Imran | |
| 5,284,142 A | 2/1994 | Goble et al. | |
| 5,297,549 A | 3/1994 | Beatty et al. | |
| 5,300,068 A | 4/1994 | Rosar et al. | |
| 5,309,910 A | 5/1994 | Edwards et al. | |
| 5,341,807 A | 8/1994 | Nardella | |
| 5,381,333 A | 1/1995 | Isaacson et al. | |
| 5,469,858 A | 11/1995 | Osborne | |
| 5,480,422 A | 1/1996 | Ben-Haim | |
| 5,499,981 A | 3/1996 | Kordis | |
| 5,500,011 A | 3/1996 | Desai | |
| 5,553,611 A | 9/1996 | Budd et al. | |
| 5,568,809 A | 10/1996 | Ben-Haim | |
| 5,577,502 A | 11/1996 | Darrow et al. | |
| 5,588,429 A | 12/1996 | Isaacson et al. | |
| 5,634,469 A | 6/1997 | Bruder et al. | |
| 5,662,108 A | 9/1997 | Budd et al. | |
| 5,687,737 A | 11/1997 | Branham et al. | |
| 5,697,377 A | 12/1997 | Wittkampf | |
| 5,704,365 A | 1/1998 | Albrecht et al. | |
| 5,722,402 A | 3/1998 | Swanson et al. | |
| 5,782,239 A | 7/1998 | Webster et al. | |
| 5,840,025 A | 11/1998 | Ben-Haim | |
| 5,840,031 A | 11/1998 | Crowley | |
| 5,846,198 A | 12/1998 | Killmann | |
| 5,848,972 A | 12/1998 | Triedman et al. | |
| 5,871,443 A | 2/1999 | Edwards et al. | |
| 5,893,847 A | 4/1999 | Kordis | |
| 5,896,847 A | 4/1999 | Usuki | |
| 5,921,982 A | 7/1999 | Lesh et al. | |
| 5,928,228 A | 7/1999 | Kordis et al. | |
| 5,954,665 A | 9/1999 | Ben-Haim | |
| 5,957,958 A | 9/1999 | Schulman et al. | |
| 5,971,933 A | 10/1999 | Gopakumaran et al. | |
| 5,983,126 A | 11/1999 | Wittkampf | |
| 5,986,126 A | 11/1999 | Bunel et al. | |
| 6,014,581 A | 1/2000 | Whayne et al. | |
| 6,050,267 A | 4/2000 | Nardella et al. | |
| 6,095,150 A | 8/2000 | Panescu et al. | |
| 6,163,716 A | 12/2000 | Edwards et al. | |
| 6,167,296 A | 12/2000 | Shahidi | |
| 6,226,542 B1 | 5/2001 | Reisfeld | |
| 6,236,886 B1 | 5/2001 | Cherepenin et al. | |
| 6,240,307 B1 | 5/2001 | Beatty et al. | |
| 6,246,898 B1 | 6/2001 | Vesely et al. | |
| 6,254,536 B1 | 7/2001 | DeVito | |
| 6,278,894 B1 | 8/2001 | Salo et al. | |
| 6,298,257 B1 | 10/2001 | Hall et al. | |
| 6,308,093 B1 | 10/2001 | Armoundas et al. | |
| 6,314,310 B1 | 11/2001 | Ben-Haim et al. | |
| 6,317,619 B1 | 11/2001 | Boernert et al. | |
| 6,318,375 B1 | 11/2001 | Plicchi et al. | |
| 6,360,123 B1 | 3/2002 | Kimchi et al. | |
| 6,368,285 B1 | 4/2002 | Osadchy et al. | |
| 6,400,981 B1 | 6/2002 | Govari | |
| 6,516,807 B1 | 2/2003 | Panescu et al. | |
| 6,547,082 B1 | 4/2003 | Babini | |
| 6,556,695 B1 | 4/2003 | Packer et al. | |
| 6,574,492 B1 | 6/2003 | Ben-Haim et al. | |
| 6,574,498 B1 | 6/2003 | Gilboa | |
| 6,593,884 B1 | 7/2003 | Gilboa et al. | |
| 6,600,948 B2 | 7/2003 | Ben-Haim et al. | |
| 6,603,996 B1 | 8/2003 | Beatty et al. | |
| 6,631,290 B1 | 10/2003 | Guck et al. | |
| 6,640,119 B1 | 10/2003 | Budd et al. | |
| 6,650,927 B1 | 11/2003 | Keidar | |
| 6,690,963 B2 | 2/2004 | Ben-Haim et al. | |
| 6,701,176 B1 | 3/2004 | Halperin et al. | |
| 6,728,562 B1 | 4/2004 | Budd et al. | |
| 6,773,402 B2 | 8/2004 | Govari et al. | |
| 6,807,439 B2 | 10/2004 | Edwards et al. | |
| 6,839,588 B1 | 1/2005 | Rudy | |
| 6,847,839 B2 | 1/2005 | Ciaccio et al. | |
| 6,872,428 B2 | 3/2005 | Yang et al. | |
| 6,873,872 B2 | 3/2005 | Gluckman et al. | |
| 6,892,090 B2 | 5/2005 | Verard et al. | |
| 6,892,091 B1 | 5/2005 | Ben-Haim et al. | |
| 6,893,588 B2 | 5/2005 | Lawson et al. | |
| 6,939,309 B1 | 9/2005 | Beatty et al. | |
| 6,957,101 B2 | 10/2005 | Porath et al. | |
| 6,978,168 B2 | 12/2005 | Beatty et al. | |
| 6,990,370 B1 | 1/2006 | Beatty et al. | |
| 7,016,719 B2 | 3/2006 | Rudy et al. | |
| 7,043,292 B2 | 5/2006 | Tarjan et al. | |
| 7,127,301 B1 * | 10/2006 | Okandan | A61N 1/0543 607/116 |
| 7,198,635 B2 | 4/2007 | Danek et al. | |
| 7,263,397 B2 | 8/2007 | Hauck et al. | |
| 7,505,810 B2 | 3/2009 | Harlev et al. | |
| 7,515,954 B2 | 4/2009 | Harlev et al. | |
| 7,571,011 B2 | 8/2009 | Zhou et al. | |
| 7,729,752 B2 | 6/2010 | Harlev et al. | |
| 8,103,327 B2 | 1/2012 | Harlev et al. | |
| 8,137,343 B2 | 3/2012 | Harlev et al. | |
| 8,364,235 B2 | 1/2013 | Kordis et al. | |
| 8,447,377 B2 | 5/2013 | Harlev et al. | |
| 8,463,368 B2 | 6/2013 | Harlev et al. | |
| 8,538,509 B2 | 9/2013 | Harlev et al. | |
| 8,725,240 B2 | 5/2014 | Harlev et al. | |
| 8,825,130 B2 | 9/2014 | Just et al. | |
| 8,849,369 B2 | 9/2014 | Cogan et al. | |
| 9,014,793 B2 | 4/2015 | Harlev et al. | |
| 2002/0022137 A1 * | 2/2002 | Breme | C23C 16/18 428/457 |
| 2002/0151807 A1 | 10/2002 | Goldin | |
| 2002/0177766 A1 | 11/2002 | Mogul | |
| 2003/0018251 A1 | 1/2003 | Solomon | |
| 2003/0065271 A1 | 4/2003 | Khoury | |
| 2003/0076277 A1 | 4/2003 | Muramatsu et al. | |
| 2003/0078509 A1 | 4/2003 | Panescu | |
| 2003/0216630 A1 | 11/2003 | Jersey-Willuhn et al. | |
| 2004/0077942 A1 | 4/2004 | Hall et al. | |
| 2004/0097806 A1 | 5/2004 | Hunter et al. | |
| 2004/0220652 A1 | 11/2004 | Zhou et al. | |
| 2004/0243015 A1 | 12/2004 | Smith et al. | |
| 2004/0254437 A1 | 12/2004 | Hauck et al. | |
| 2005/0033136 A1 | 2/2005 | Govari et al. | |
| 2005/0038337 A1 | 2/2005 | Edwards | |
| 2005/0054918 A1 | 3/2005 | Sra | |
| 2005/0107834 A1 | 5/2005 | Freeman et al. | |
| 2005/0154282 A1 | 7/2005 | Li et al. | |
| 2005/0288599 A1 | 12/2005 | MacAdam et al. | |
| 2006/0085049 A1 | 4/2006 | Cory et al. | |
| 2006/0115323 A1 * | 6/2006 | Coppeta | A61K 9/0097 403/270 |
| 2006/0116575 A1 | 6/2006 | Willis | |
| 2006/0122526 A1 | 6/2006 | Berenfeld et al. | |
| 2006/0148254 A1 * | 7/2006 | McLean | C23C 14/5853 438/686 |
| 2006/0173251 A1 | 8/2006 | Govari et al. | |

(56) References Cited

U.S. PATENT DOCUMENTS

| | | |
|---|---|---|
| 2006/0178587 A1 | 8/2006 | Khoury |
| 2006/0241401 A1 | 10/2006 | Govari et al. |
| 2007/0016007 A1 | 1/2007 | Govari et al. |
| 2007/0038078 A1 | 2/2007 | Osadchy |
| 2007/0049821 A1 | 3/2007 | Willis |
| 2007/0083194 A1 | 4/2007 | Kunis et al. |
| 2007/0128420 A1* | 6/2007 | Maghribi ............... A61L 27/48 |
| | | 428/221 |
| 2007/0197929 A1 | 8/2007 | Porath et al. |
| 2007/0265539 A1 | 11/2007 | Hastings et al. |
| 2007/0270703 A1 | 11/2007 | He et al. |
| 2007/0287902 A1 | 12/2007 | Fuimaono et al. |
| 2007/0299351 A1 | 12/2007 | Harlev et al. |
| 2007/0299352 A1 | 12/2007 | Harlev et al. |
| 2007/0299353 A1 | 12/2007 | Harlev et al. |
| 2008/0190438 A1 | 8/2008 | Harlev et al. |
| 2008/0221566 A1 | 9/2008 | Krishnan |
| 2008/0234588 A1 | 9/2008 | Feldman et al. |
| 2008/0249424 A1 | 10/2008 | Harlev et al. |
| 2009/0171274 A1 | 7/2009 | Harlev et al. |
| 2009/0177072 A1 | 7/2009 | Harlev et al. |
| 2009/0253976 A1 | 10/2009 | Harlev et al. |
| 2009/0293270 A1 | 12/2009 | Brindley et al. |
| 2009/0299355 A1 | 12/2009 | Bencini et al. |
| 2010/0230285 A1 | 9/2010 | Hoss et al. |
| 2010/0286551 A1 | 11/2010 | Harlev et al. |
| 2012/0277567 A1 | 11/2012 | Harlev et al. |
| 2012/0296405 A1 | 11/2012 | Thenuwara et al. |
| 2013/0172715 A1 | 7/2013 | Just et al. |
| 2013/0253298 A1 | 9/2013 | Harlev et al. |
| 2013/0274582 A1 | 10/2013 | Afonso et al. |
| 2013/0345538 A1 | 12/2013 | Harlev et al. |
| 2014/0018880 A1 | 1/2014 | Zarins et al. |
| 2014/0046401 A1 | 2/2014 | Chen et al. |
| 2014/0200442 A1 | 7/2014 | Harlev et al. |
| 2014/0262462 A1 | 9/2014 | Shah et al. |
| 2014/0275921 A1 | 9/2014 | Harlev et al. |
| 2015/0223726 A1 | 8/2015 | Harlev |
| 2015/0342491 A1 | 12/2015 | Marecki et al. |
| 2015/0351652 A1 | 12/2015 | Marecki et al. |

FOREIGN PATENT DOCUMENTS

| | | |
|---|---|---|
| EP | 0779059 B1 | 6/1997 |
| EP | 1484026 A1 | 12/2004 |
| EP | 2265172 A2 | 12/2010 |
| EP | 2269505 B1 | 5/2012 |
| WO | WO199725917 A1 | 7/1997 |
| WO | 2008097767 A2 | 8/2008 |
| WO | 2009085108 A1 | 7/2009 |
| WO | 2009123819 A2 | 10/2009 |
| WO | 2013028998 A2 | 2/2013 |
| WO | 2014110579 A1 | 7/2014 |
| WO | 2015187386 A1 | 12/2015 |
| WO | 2015187430 A2 | 12/2015 |

OTHER PUBLICATIONS

Adams et al., "Seeded Region Growing", IEEE Transactions on Pattern Analysis and Machine Intelligence, 16(6):641-647, 1994.

Arthur, "Clinical Use of Intracardiac Impedance: Current Applications and Future Perspectives", PACE, vol. 24:500-506, Apr. 2001.

Authorized officer Carl H. Layno, International Search Report and the Written Opinion in PCT/US07/70854 dated Sep. 12, 2008, 15 pages.

Authorized officer, Blaine R. Copenheaver, International Search Report and the Written Opinion in PCT/US2009/061277 dated Apr. 8, 2010, 13 pages.

Baan, Jan et al., "Continuous Measurement of Left Ventricular Volume In Animals and Humans by Conductance Catheter", Circulation, 07(5):812-823, 1984.

Badics, "Real-Time Reconstruction of Endocardial Potential Maps in Non-Contact Cardiace Mapping", International Journal for computation and Mathematics in Electrical Engineering (COMPEL), vol. 28, No. 4, 2009.

Ben-Haim et al., "Nonfluoroscopic, in Vivo Navigation and Mapping Technology", Nature Medicine, 2(12):1393-1395, 1996.

Besl et al., "A Method for Registration of 3-D Shapes", IEEE Transaction on Pattern Analysis and Machine Intelligence, 14(2):239-256, 1992.

Blomstrom-Lundqvist et al., "ACC/AHA/ESC Guidelines for the Management of Patients with Supraventricular Arrhythmias-Executive Summary", Journal of the American College of Cardiology, 42(8):1493-1531, 2003.

Breithardt et al., "AHA Medical/Scientific Statement—Special Report: Standards for Analysis of Ventricular Late Potentials Using High-Resolution or Signal/Averaged Electrocardiography", Circulation, 83(4):1481-1488, 1991.

Brooks et al., "Electrical Imaging of the Heart", IEEE Signal Processing Magazine, pp. 24-42, 1997.

Caspi et al., "Stem Cell Research: Regenerating the Heart Using Human Embryonic Stem Cells—from Cell to Bedside", IMAJ 8:208-214, 2006.

Cheney et al, "Electrical Imedance Tomography," SIAM Review 41, pp. 85-101, 1999.

Communication pursuant to Article 94(3) EPC in European Application No. 07798369, dated Nov. 17, 2011, 5 pages (0002EP1).

De Groot et al., "Three-Dimensional Catheter Positioning During Radiofrequency Ablation in Patients: First Application of a Real-Time Position Management System", Journal of Cardiovascular Electrophysiology, 11:1183-1192, 2000.

Donahue et al., "Focal Modification of Electrical Conduction in the Heart by Viral Gene Transfer", Nature Medicine, 6(12):1395-1398, 2000.

Dong et al., "Integrated Electroanatomic Mapping With Three-Dimensional Computed Tomographic Images for Real- Time Guided Ablations", Circulation 113:186-194, 2006.

Durrer et al., "Total Excitation of the Isolated Human Heart", Circulation, XL1:899-912, 1970.

Ector, Joris et al., "Cardiac Three-Dimensional Magnetic Resonance Imaging and Fluoroscopy Merging", Circulation, 112:3769-3776, 2005.

European Search Report issued in EP Application No. 12815179.2, dated Apr. 28, 2015, 6 pages.

Extended European Search Report issued in EP Application No. 09727423.7, dated May 15, 2012, 5 pages.

Friedman, "Catheter Cryoablation of Cardiac Arrhythmias", Current Opinion in Cardiology, 20:48-54, 2005.

Friedman, "Novel Mapping Techniques for Cardiac Electrophysiology", Heart, 87:575-582, 2002.

Geddes et al., "Criteria for the Selection of Materials for implanted Electrodes," Annals of Biomedical Engineering 31:879-890, 2003.

Gepstein et al., "A Novel Method for Nonfluoroscopic Catheter-Based Electroanatomical Mapping of the Heart", Circulation 95:1611-1622, 1997.

Haug. E. J. et al.: Design Sensitivity Analysis of Structural Systems, Mathematics in Science and Engineering, vol. 177 (1986).

Huang, Y-Chih et al., "Development of a Third Generation Intraventricular Impedance Imaging (III) System Evaluation of Hardware Design", Engineering in Medicine and Biology Society, Proceedings of the 19th Annual Internal Conference of the IEEE/EMBS, 6:2442-2444 Oct. 30-Nov. 2, 1997.

International Preliminary Report on Patentability issued in PCT/US2008/013553, dated Feb. 5, 2009, 6 pages.

International Preliminary Report on Patentability issued in PCT/US2008/052385, dated Aug. 8, 2008, 6 pages.

International Preliminary Report on Patentability issued in PCT/US2009/036099, dated Oct. 14, 2010, 20 pages.

International Preliminary Report on Patentability issued in PCT/US2014/060137, dated Apr. 28, 2016, 9 pages.

International Search Report and the Written Opinion in PCT/US08/52385 dated Aug. 8, 2008, 11 pages.

International Search Report and Written Opinion issued in PCT/US2009/036099, dated Apr. 28, 2009, 21 pages.

(56) References Cited

OTHER PUBLICATIONS

International Search Report and Written Opinion issued in PCT/US2014/060137, dated Dec. 10, 2014, 11 pages.
International Search Report and Written Opinion issued in PCT/US2015/032004, dated Sep. 4, 2015, 8 pages.
International Search Report and Written Opinion issued in PCT/US2015/032753, dated Mar. 9, 2016, 17 pages.
Jain et al., "Cell Therapy Attenuates Deleterious Ventricular Remodeling and improves Cardiac Performance after Myocardial Infarction", Circulation, 103:1920-1927, 2001.
Jalife, "Rotors and Spiral Waves in Atrial Fibrillation", Journal of Cardiovascular Electrophysiology, 14:776-780, 2003.
Jane et al., Alignment Methods for Averaging of High-Resolution Cardiac Signals: A Comparative Study of Performance, IEEE Transaction on Biomedical Engineering, 38(6):571-579, 1991.
Jia et al., "Electrophysiologic Endocardial Mapping from a Noncontact Nonexpandable Catheter: A Validation Study of a Geometry-Based Concept". Journal of Cardiovascular Electrophysiology, 11:1238-1251, 2000.
Kikuchi et al., "Targeted Modification of Atrial Electrophysiology by Homogeneous Transmural Artial Gene Transfer", Circulation, 111:264-270, 2005.
Kistler et al., "Validation of Three-Dimensional Cardiac Image Integration: Use of Integrated CT Image into Electroanatomic Mapping System to Performa Catheter Ablation of Atrial Fibrillation", Journal of Cardiovascular Electrophysiology, 17:341-348, 2006.
Kuklik et al., The reconstruction, from a set of points, and analysis of the interior surface of the heart chamber, Physiological Measurement 25, pp. 617-627, 2004.
Kun, Stevan et al., "Conductance Volumetric Model of an Eccentrically Positioned Catheter within a Three-Compartment Ellipsoidal Ventricle", U, IEEE Transactions on Jun. 1993, 40(6); 589-592.
L. Piegl, W. Tiller: The NURBS Book, 2nd Edition, Springer (1997).
Anderson, David J., et al. "Batch-Fabricated Thin-Film Electrodes for Stimulation of the Central Auditory System." IEEE Transactions on Biomedical Engineering, 36(7):693-704, Jul. 1989.
Bak, M., et al. "Visual Sensations Produced by Intracortical Microstimulation of the Human Occipital Cortex." Medical & Biological Engineering & Computing, 28:257-259, May 1990.
Liu, Xindong, et al. "Stability of the Interface Between Neural Tissue and Chronically Implanted Microelectrodes." Intracortical IEEE Transactions on Rehabilitation Engineering, 7(3):315-326, Sep. 1999.
Loeb, G. E., et al. "Toward the Ultimate Metal Microelectrode." Journal of Neuroscience Methods, 63:175-183, 1995.
McCreery, D.B., et al. "Stimulation With Chronically Implanted Microelectrodes in the Cochlear Nucleus of the Cat: Histologic and Physiologic Effects." Hearing Research, 62:42-56, 1992.
Meyer, Ross D., et al. "Electrodeposited Iridium Oxide for Neural Stimulation and Recording Electrodes." IEEE Transactions on Neural Systems and Rehabilitation Engineering, 9(1):2-11, Mar. 2001.
Robblee, L.S., et al. "Activated IR: An Electrode Suitable for Reversible Charge Injection in Saline Solution." Journal of the Electrochemical Society, 130(3), (1983), 731-733.
International Search Report and Written Opinion issued in PCT/US2016/047328, dated Nov. 11, 2016, 12 pages.
Laciar et al., "improved Alignment Method for Noisy High-Resolution ECG and Holter Records Using Multiscale Cross-Correlation", IEEE Transactions on Biomedical Engineering, 50(3):344-353, 2003.
Liu et al., "Endocardial Potential Mapping from a Noncontact Nonexpandable Catheter: A Feasibility Study", Annals of Biomedical Engineering, 26:994-1009, 1998.
Lorensen et al., "Marching Cubes: A High Resolution 3D Surface Construction Algorithm", Computer Graphics 21(4):163-169, Jul. 1987.
Makela et al., "A Review of Cardiac Image Registration Methods", IEEE Transaction on Medical Imaging, 21(9):1011-1021, 2002.
Malladi, R. et al., "A Geometric Approach to Segmentation and Analysis of 3D Medical Images", Mathematical Methods in Biomedical Image Analysis, Proceedings of the Workshop on, Jun. 21-22, 1996, pp. 244-252.
Mangan, Alan et al., "Partitioning 3D Surface Meshes Using Watershed Segmentation", IEEE Transactions on Visualization and Computer Graphics, 5(4):308-321, 1999.
Meininger et al., "Initial Experience with a Novel Focused Ultrasound Ablation System for Ring Ablation Outside the Pulmonary Vein", Journal of Interventional Cardiac Electrophysiology, 8:141-148, 2003.
Merrill, Daniel R. et al., "Electrical stimulation of excitable tissue: design of efficacious and safe protocols", Journal of Neuroscience Methods, 141:171-198, 2005.
Miller, "Editor's Forum—Application of Registration for Ablation: A Marriage of Technologies", Journal of Interventional Cardiac Electrophysiology, 11:87-89, 2004.
Nademanee et al., "A New Approach for Catheter Ablation of Atrial Fibrillation: Mapping of the Electrophysiologic Substrate", Journal of the American College of Cardiology, 43(11):2044-2053, 2004.
Non-Final Office Action in U.S. Appl. No. 11/451,908, dated Sep. 4, 2008, 12 pages.
Non-Final Office Action issued in U.S. Appl. No. 11/451,898 dated Sep. 25, 2008, 13 pages.
Noseworthy et al., "The Impact of Respiration on Left Atrial and Pulmonary Venous Anatomy: Implications for Image- Guided Intervention", Heart Rhythm, 2:1173-1178, 2005.
Pappone et al., "Robotic Magnetic Navigation for Atrial Fibrillation Ablation", Journal of the American College of Cardiology, 47(7): 1390-1400, 2006.
Paragios, "A Level Set Approach for Shape-Driven Segmentation and Tracking of the Left Ventricle", IEEE Transactions on Medical Imaging, 22(6):773-776, 2003.
Persson et al., "A Simple Mesh Generator in MATLAB", SIAM Review, 46(2):329-345, 2004.
Persson, "Mesh Generation for Implicit Geometrics", Massachusetts Institute of Technology—Thesis, Feb. 2005.
Pham, Dzung, et al., "Current Methods in Medical Image Segmentation", Annu. Rev. Biomed. Eng., 02:315-337, 2000.
Rao et al., "Novel Noncontact Catheter System for Endocardial Electrical and Anatomical imaging", Annals of Biomedical Engineering, 32(4):573-584, 2004.
Reddy et al., "Use of a Diode Laser Balloon Ablation Catheter to Generate Circumferential Pulmonary Venous Lesions in an Open-Thoracotomy Caprine Model", PACE, 27:52-57, 2004.
Reddy et al., "Integration of Cardiac Meagnetic Resonance Imaging with Three-Dirnentional Electroanatomic Mapping to Guide Left Ventricular Catheter Manipulation—Feasibility is a Porcine Modelof Healed Myocardial Infarction", Journal of the American College of Cardiology, 44(11):2202-2213, 2004.
Sanders et al., "Spectral Analysis Identifies Sites of High-Frequency Activity Maintaining Atrial Fibrillation in Humans", Circulation, 112:789-797, 2005.
Sethian; "Level Set Methods and Fast Marching Methods: Evolving Interfaces in Computational Geometry; Fluid Mechanics, Computer Vision, and Materials Science", Department of Mathematics—University of California, Berkeley, Cambridge University Press, 1999.
Simon et al. "Electroanatomic Mapping of the Right Atrium With a Right Atrial Basket Catheter and Three-Dimensional Intracardiac Echocardiography", PACE, 27: 318-326, 2004.
Smits et al., "Catheter-Based Intramyocarial Injection of Autologous Skeletal Myoblasts as a Primary Treatment of Ischemic Heart Failure", Journal of the American College of Cardiology, 42(12):2063-2069, 2003.
Solomon et al., "Real-Time Cardiac Catheter Navigation on Three-Dimensional CT Images", Journal of Interventional Cardiac Electrophysiology, 8:27-36, 2003.
Sra et al., "Registration of Three-Dimensional Left Atrial Computed Tomographic Images With Projection Images Obtained Using Fluoroscopy", Circulation, 112:3763-3768, 2005.

(56) References Cited

OTHER PUBLICATIONS

Sra, Jasbir et al, "Registration of 3D Computed Tomographic Images With Interventional Systems: Implications For Catheter Ablation of Atrial Fibrillation", J Interv Card Electrophysiol, 16:141-148; 2006.
Stevenson, "Radiofrequency Catheter Ablation of Ventricular Tachycardia After Myocardial Infarction", Circulation, 98:308-314, 1998.
Taccardi et al., "A New Intracavitary Probe for Detecting the Site of the Origin of Ectopic Ventricular Beats During One Cardiac Cycle", Circulation, 75(1):272-281, 1987.
Thal et al., "Novel Applications in Catheter Ablation", Journal of Interventional Cardiac Electrophysiology, 13:17-21, 2005.
Thiagalingam et al., "Noncontact Mapping of the Left Ventricle: Insights from Validation With Transmural Contact Mapping", PACE, 27:570-578, 2004.
Voth, "The Inverse Problem of Electrocardiography: Industrial Solutions and Simulations", BEM and NFSI Conference Proceedings, Minneapolis, MN, May 12-15, 2005, pp. 191-194.
Wittkampf et al., "LocaLisa: New Technique for Real-Time 3-Dimensional Localization of Regular Intracardiac Electrodes", Circulation, 99:1312-1317, 1999.
Written Opinion of the International Searching Authority issued in PCT/US208/13553, dated Feb. 5, 2009, 6 pages.
Yezzi, Anthony et al., "A Geometric Snake Model for Segmentation", IEEE Transactions on Medical Imaging, 16(2) Apr. 1997.

\* cited by examiner

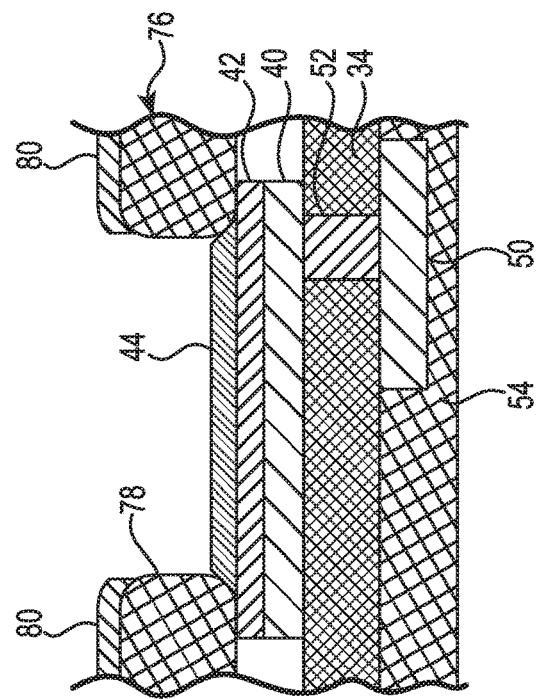
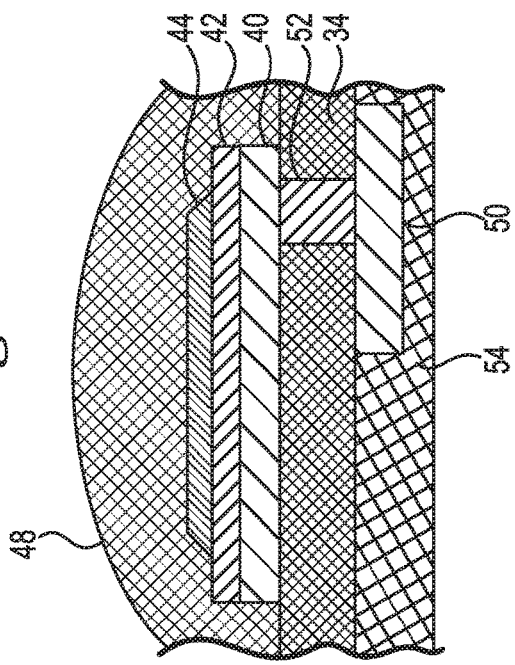
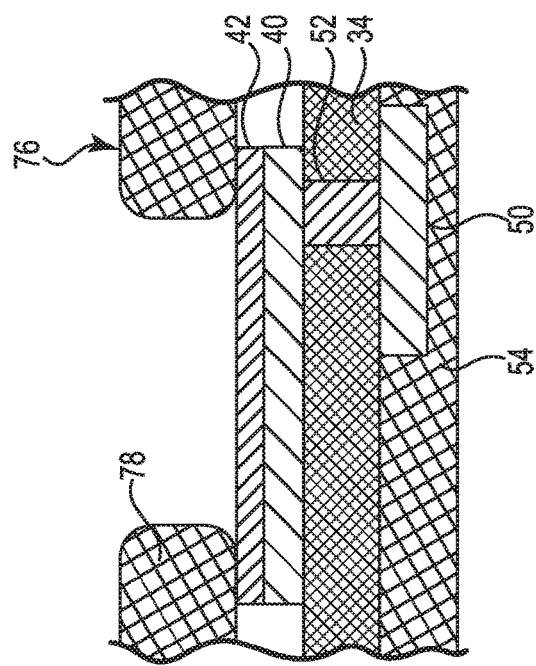
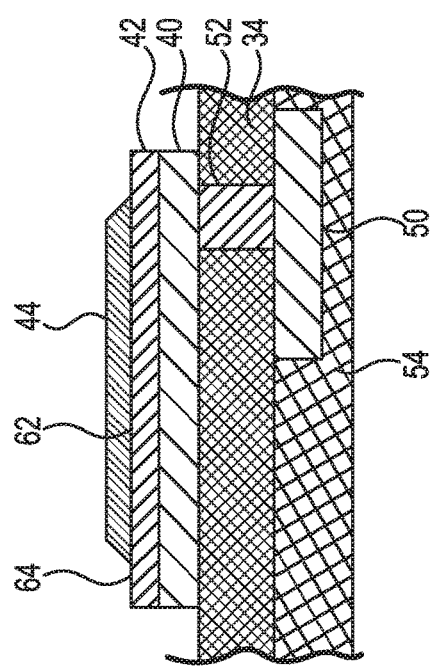
Fig. 5
Fig. 6
Fig. 7
Fig. 8

FLEXIBLE ELECTRODE FOR CARDIAC SENSING AND METHOD FOR MAKING

CROSS-REFERENCE TO RELATED APPLICATION

This application claims priority to Provisional Application No. 62/207,814, filed Aug. 20, 2015, which is herein incorporated by reference in its entirety.

TECHNICAL FIELD

The present invention relates to cardiac signal sensing devices. More specifically, the invention relates to flexible electrodes and methods for making flexible electrodes for use in a cardiac mapping catheter.

BACKGROUND

Cardiac arrhythmias may lead to heart disease and death. Arrhythmias may be treated by medication, implantable devices, or by the ablation of specific heart tissue found to be causing arrhythmia. Ablation may be performed by a number of techniques, including the local application of energy, for example, radio frequency energy, or by the application of cryogenic temperatures to the site of the problem tissue.

The specific heart tissue responsible for arrhythmia in a patient may be identified by moving a mapping catheter having one or more electrodes around the interior of the heart and measuring cardiac signals to sense changes in the electrical fields. A map of the electrical conductivity of the heart may be formed from the measurements to identify abnormalities which may be candidates for ablation. Some mapping catheters are designed such that the electrodes may physically contact the heart wall, including flexible designs that are inserted in a compact form and later deployed into a basket-like array. Such an array is deployed after entrance into the heart, and undeployed upon completion of the mapping and prior to removal from the heart.

A mapping catheter having multiple electrodes which must be deployed and undeployed within the heart may benefit from an improved electrode structure.

SUMMARY

Example 1 is an electrode for cardiac signal sensing, the electrode including a conductive layer, an intermediate layer, an iridium-containing layer, an iridium oxide layer, and an insulating polymer layer. The conductive layer is formed on a portion of a flexible polymer substrate. The intermediate metal layer has a first portion and a second portion, and is formed on the conductive layer. The iridium-containing layer has a first portion and a second portion, and formed on the first portion of the intermediate metal layer. The iridium-containing layer includes at least 50 wt. % iridium. The iridium oxide layer is formed on the first portion of the iridium-containing layer. The insulating polymer layer is formed on the second portion of the intermediate metal layer and the second portion of the iridium-containing layer. The iridium-containing layer is not formed on the second portion of the intermediate metal layer; and the iridium oxide layer is not formed on the second portion of the iridium-containing layer.

In Example 2, the electrode of Example 1, wherein the iridium-containing layer consists of between 50 wt. % and 99 wt. % iridium, and the balance is platinum.

In Example 3, the electrode of Example 1, wherein the iridium-containing layer includes at least 99 wt. % iridium.

In Example 4, the electrode of any of Examples 1-3, wherein the insulating polymer layer is a parylene polymer.

In Example 5, the electrode of Example 4, wherein the parylene polymer is selected from the group consisting of poly(p-xylylene), poly(monochloro-p-xylylene), and poly(dichloro-p-xylylene).

In Example 6, the electrode of Example 5, wherein the parylene polymer is poly(monochloro-p-xylylene).

In Example 7, the electrode of any of Examples 1-6, wherein the intermediate metal layer includes gold.

Example 8 is a cardiac mapping catheter including an elongate catheter body and a plurality of splines projecting from an end of the catheter body. The splines are flexibly deployable between a radially retracted position and radially extended position. Each of the splines includes a flexible polymer substrate and a plurality of electrodes formed on the flexible polymer substrate, wherein each of the electrodes is according to any of claims 1-7.

Example 9 is a method for making an electrode for cardiac signal sensing, the electrode formed on a flexible polymer substrate having a conductive layer and an intermediate metal layer disposed on the conductive layer. The method includes depositing an iridium-containing layer onto a portion of the intermediate metal layer, depositing an insulating polymer layer, removing the insulating polymer layer from a portion of the iridium-containing layer to form a exposed surface, and electrochemically oxidizing at least a portion of the iridium-containing layer at the exposed surface to form an iridium oxide layer on the iridium-containing layer. The iridium-containing layer includes at least 50 wt. % iridium. The insulating polymer layer is deposited on the flexible polymer substrate, the conductive layer, the intermediate layer, and the iridium-containing layer.

In Example 10, the method of Example 9, wherein removing the insulating polymer layer includes laser ablating the insulating polymer layer from the portion of the iridium-containing layer.

In Example 11, the method of any of Examples 9-10, wherein depositing the insulating polymer layer includes depositing a parylene polymer by vapor deposition.

In Example 12, the method of any of Examples 9-11, wherein depositing the iridium-containing layer includes applying a first mechanical mask to the substrate, depositing the iridium-containing layer by sputter deposition, and removing the first mechanical mask. The first mechanical mask includes a first opening aligned with the intermediate metal layer to define the portion of the intermediate metal layer.

In Example 13, the method of any of Examples 9-12, wherein removing the insulating polymer layer includes applying a second mechanical mask to the substrate, laser ablating the insulating polymer layer from the portion of the iridium-containing layer; and removing the second mechanical mask. The second mechanical mask includes a second opening aligned with the portion of the iridium-containing layer, wherein the second opening is smaller than the first opening.

In Example 14, the method of any of Examples 9-12, wherein removing the insulating polymer layer includes applying a second mechanical mask to the substrate, laser ablating the insulating polymer layer from the portion of the iridium-containing layer; and removing the second mechanical mask. The second mechanical mask includes a second opening aligned with the portion of the iridium-containing layer, wherein the second opening is about the same size as the first opening.

In Example 15, the method of any of Examples 9-14, wherein electrochemically oxidizing includes immersing the substrate in an electrolytic solution, cycling the iridium-containing layer between positive and negative voltages until a desired thickness of iridium oxide is formed on the surface of the portion of iridium-containing layer, and removing the substrate from the electrolytic solution.

Example 16 is an electrode for cardiac signal sensing, the electrode including a conductive layer, an intermediate layer, an iridium-containing layer, an iridium oxide layer, and an insulating polymer layer. The conductive layer is formed on a portion of a flexible polymer substrate. The intermediate metal layer has a first portion and a second portion, and is formed on the conductive layer. The iridium-containing layer has a first portion and a second portion, and formed on the first portion of the intermediate metal layer. The iridium-containing layer includes at least 50 wt. % iridium. The iridium oxide layer is formed on the first portion of the iridium-containing layer. The insulating polymer layer is formed on the second portion of the intermediate metal layer and the second portion of the iridium-containing layer. The iridium-containing layer is not formed on the second portion of the intermediate metal layer, and the iridium oxide layer is not formed on the second portion of the iridium-containing layer.

In Example 17, the electrode of Example 16, wherein the iridium-containing layer consists of between 50 wt. % and 99 wt. % iridium, and the balance is platinum.

In Example 18, the electrode of Example 16, wherein the iridium-containing layer includes at least 99 wt. % iridium.

In Example 19, the electrode of any of Examples 16-18, wherein the intermediate metal layer includes gold.

In Example 20, the electrode of any of Examples 16-19, wherein the conductive layer includes copper.

In Example 21, the electrode of any of Examples 16-20, wherein the insulating polymer layer is a parylene polymer.

In Example 22, the electrode of Example 21, wherein the parylene polymer is selected from the group consisting of poly(p-xylylene), poly(monochloro-p-xylylene), and poly(dichloro-p-xylylene).

In Example 23, the electrode of Example 22, wherein the parylene polymer is poly(monochloro-p-xylylene).

Example 24 is a method for making an electrode for cardiac signal sensing, the electrode formed on a flexible polymer substrate having a conductive layer and an intermediate metal layer disposed on the conductive layer. The method includes depositing an iridium-containing layer onto a portion of the intermediate metal layer, depositing an insulating polymer layer, removing the insulating polymer layer from a portion of the iridium-containing layer to form a exposed surface, and electrochemically oxidizing at least a portion of the iridium-containing layer at the exposed surface to form an iridium oxide layer on the iridium-containing layer. The iridium-containing layer includes at least 50 wt. % iridium. The insulating polymer layer is deposited on the flexible polymer substrate, the conductive layer, the intermediate layer, and the iridium-containing layer.

In Example 25, the method of Example 24, wherein removing the insulating polymer layer includes laser ablating the insulating polymer layer from the portion of the iridium-containing layer.

In Example 26, the method of any of Examples 24-25, wherein depositing the insulating polymer layer includes depositing a parylene polymer by vapor deposition.

In Example 27, the method of Example 26, wherein the parylene polymer is poly(monochloro-p-xylylene).

In Example 28, the method of any of Examples 24-27, wherein the intermediate metal layer includes gold.

In Example 29, the method of any of Examples 24-28, wherein depositing the iridium-containing layer includes applying a first mechanical mask to the substrate, depositing the iridium-containing layer by sputter deposition, and removing the first mechanical mask. The first mechanical mask includes a first opening aligned with the intermediate metal layer to define the portion of the intermediate metal layer.

In Example 30, the method of any of Examples 24-29, wherein removing the insulating polymer layer includes applying a second mechanical mask to the substrate, laser ablating the insulating polymer layer from the portion of the iridium-containing layer; and removing the second mechanical mask. The second mechanical mask includes a second opening aligned with the portion of the iridium-containing layer, wherein the second opening is smaller than the first opening.

In Example 31, the method of any of Examples 24-29, wherein removing the insulating polymer layer includes applying a second mechanical mask to the substrate, laser ablating the insulating polymer layer from the portion of the iridium-containing layer; and removing the second mechanical mask. The second mechanical mask includes a second opening aligned with the portion of the iridium-containing layer, wherein the second opening is about the same size as the first opening.

In Example 32, the method of any of Examples 24-31, wherein electrochemically oxidizing includes immersing the substrate in an electrolytic solution, cycling the iridium-containing layer between positive and negative voltages until a desired thickness of iridium oxide is formed on the surface of the portion of iridium-containing layer, and removing the substrate from the electrolytic solution.

Example 33 is a cardiac mapping catheter including an elongate catheter body and a plurality of splines projecting from an end of the catheter body. The splines are flexibly deployable between a radially retracted position and radially extended position. Each of the splines includes a flexible polymer substrate and a plurality of electrodes formed on the flexible polymer substrate. Each of the electrodes includes a conductive layer, an intermediate layer, an iridium-containing layer, an iridium oxide layer, and an insulating polymer layer. The conductive layer is formed on a portion of a flexible polymer substrate. The intermediate metal layer has a first portion and a second portion, and is formed on the conductive layer. The iridium-containing layer has a first portion and a second portion, and formed on the first portion of the intermediate metal layer. The iridium-containing layer includes at least 50 wt. % iridium. The iridium oxide layer is formed on the first portion of the iridium-containing layer. The insulating polymer layer is formed on the second portion of the intermediate metal layer and the second portion of the iridium-containing layer. The iridium-containing layer is not formed on the second portion of the intermediate metal layer. The iridium oxide layer is not formed on the second portion of the iridium-containing layer.

In Example 34, the catheter of Example 33, wherein the iridium-containing layer includes at least 99 wt. % iridium.

In Example 35, the catheter of any of Examples 33-34, wherein the insulating polymer layer includes poly(monochloro-p-xylylene).

While multiple embodiments are disclosed, still other embodiments of the present invention will become apparent to those skilled in the art from the following detailed description and drawings, which show and describe illustrative embodiments of the invention. Accordingly, the drawings and detailed description are to be regarded as illustrative in nature and not restrictive.

BRIEF DESCRIPTION OF THE DRAWINGS

FIGS. 4-12 are schematic views showing a method for making the electrode of FIG. 3 in accordance with embodiments of the present invention.

Figure 1:
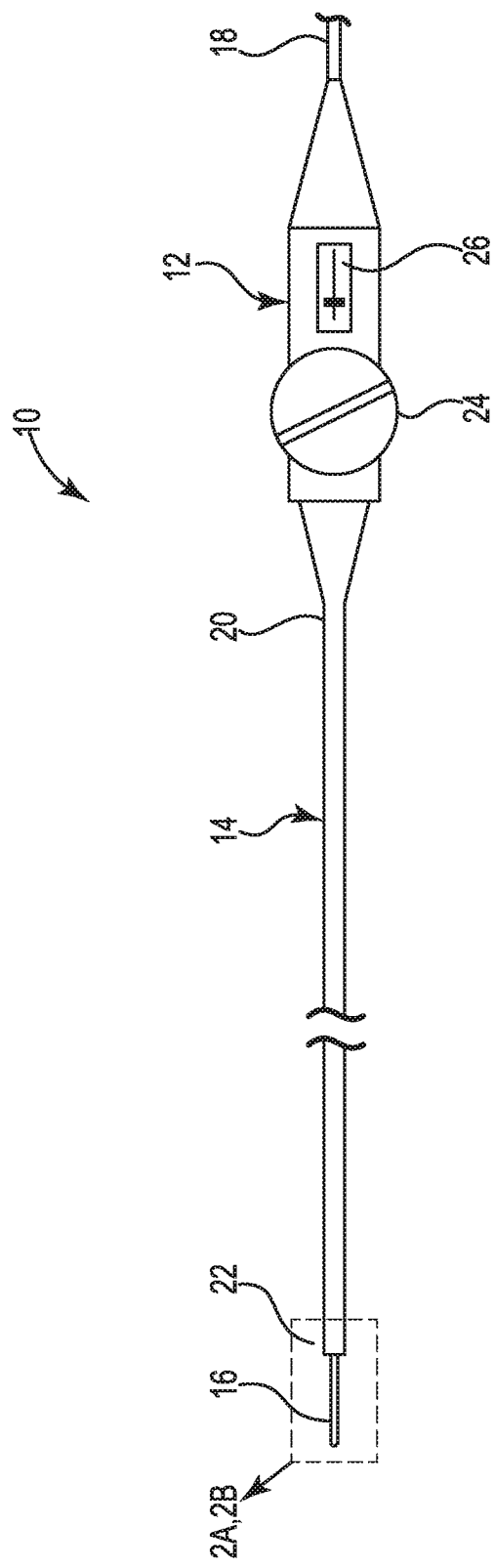
FIG. 1 is a schematic view of a cardiac mapping catheter suitable for use with embodiments of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

A more complete understanding of the present invention is available by reference to the following detailed description of numerous aspects and embodiments of the invention. The detailed description of the invention which follows is intended to illustrate but not limit the invention.

Electrodes embodying the present invention may be employed in cardiac mapping catheters as described in "CARDIAC MAPPING CATHETER" (U.S. Pat. No. 8,447,377, issued May 21, 2013), hereby incorporated by reference in its entirety. Such catheters typically have several flexible splines, each spline including a plurality of electrodes. Electrode embodiments of the present invention are able to flex while also maintaining low impedance and biocompatibility.

FIG. 1 provides an illustrative but non-limiting example of a cardiac mapping catheter 10 including electrodes embodying the present invention. As shown in FIG. 1, the cardiac mapping catheter 10 may include a handle 12, an elongate lead body 14, an electrode assembly 16, and an electrical connection 18. The lead body 14 may extend from a proximal end 20 to a distal end 22. The electrode array 16 may project from the distal end 22 of the lead body 14. The lead body 14 may be connected at the proximal end 20 to the handle 12. The electrical connection 18 may extend from the handle 12 to a mapping data recording and analysis system (not shown). The handle 12 may include an articulation control 24 and a deployment control 26.

The articulation control 24 may control bending of the distal end 22 of the lead body 14 by way of one or more articulation control elements, for example wires (not shown) extending from the articulation control 24 to the distal end 22 by way of one or more lumens (not shown) extending through the lead body 14 from the proximal end 20 to the distal end 22. Bending the distal end 22 provides for flexibility in maneuvering the electrode array 16 within a patient's heart.

The deployment control 26 may control deployment of the electrode array 16 by way of a deployment control element 28 (shown in FIG. 2B) extending from the deployment control 26 to the electrode array 16 by way of one of the lumens extending through the lead body 14. The lumens may also include a set of electrical conductors (not shown) extending from the electrode array 16 to handle 12 to connect the electrode array 16 to the mapping data recording and analysis system.

Figure 2A:
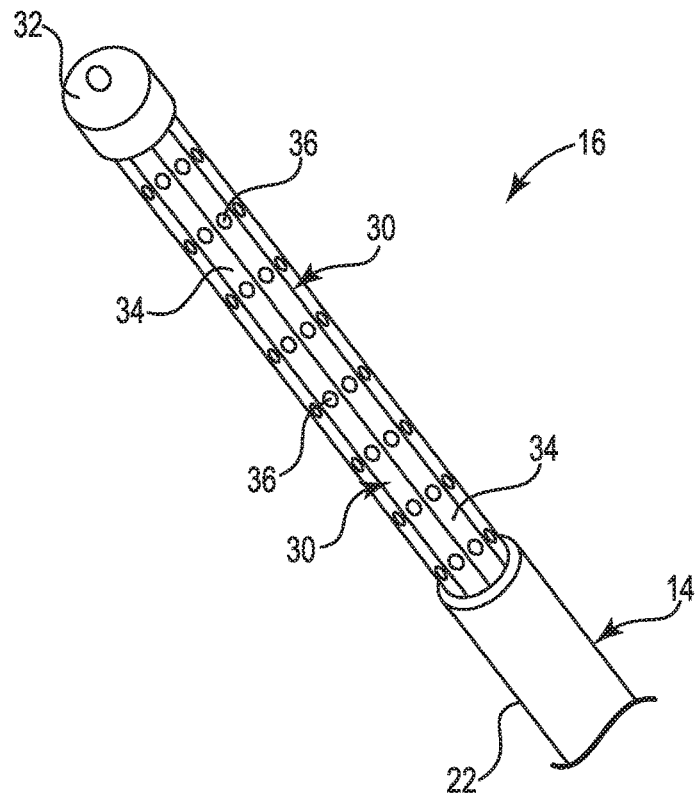
FIGS. 2A and 2B are partial perspective views showing a distal end of the mapping catheter of FIG. 1.
Figure 2B:
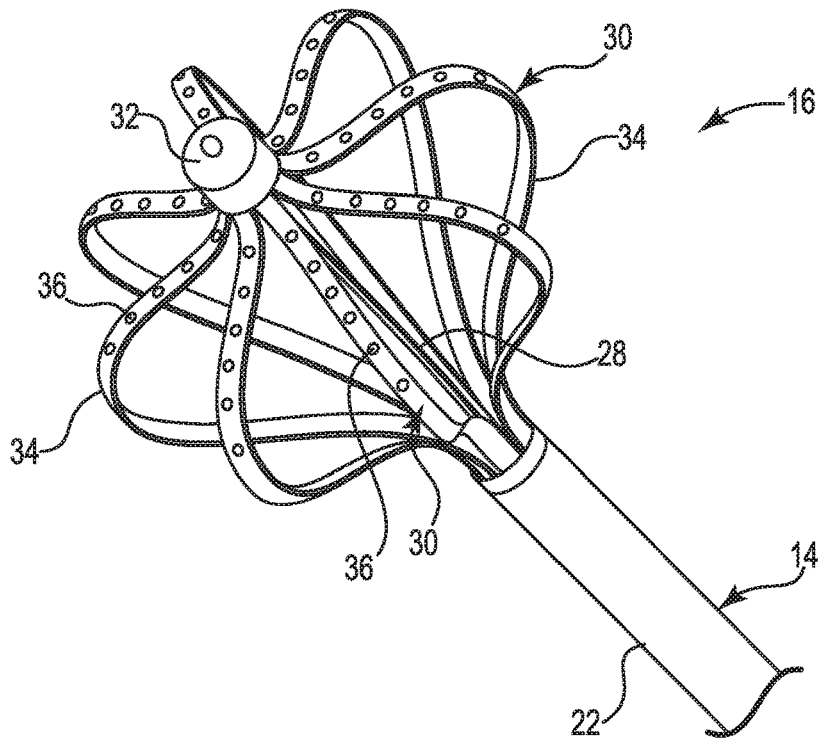

FIGS. 2A and 2B are partial perspective views showing the electrode array 16 and the distal end 22 of the cardiac mapping catheter 10 of FIG. 1. FIG. 2A shows the electrode array 16 undeployed in a radially retracted position. FIG. 2B shows the electrode array 16 deployed in a radially extended position. As shown in FIGS. 2A and 2B, the electrode array 16 may include a plurality of splines 30 and an end cap 32. Each of the plurality of splines 30 may extend between the distal end 22 and the end cap 32. Each of the splines 30 may include a flexible polymer substrate 34 and a plurality of electrodes 36. In the exemplary embodiment shown in FIGS. 2A and 2B, there are eight splines 30, each including eight electrodes 36, for a total of sixty-four electrodes in the electrode array 16. However, it is understood that embodiments may include greater or fewer than eight splines 30, and greater or fewer than eight electrodes 36 on each of the splines 30. As shown in FIG. 2B, the deployment control element 28 may extend from the end cap 32 and into the lead body 14 at the distal end 22. The deployment control element 28 may be a wire connecting the end cap 32 to the deployment control 26 (FIG. 1) such that movement of the deployment control 26 may cause the wire to move in the proximal direction and pull the end cap 32 in the proximal direction. Movement of the end cap 32 in the proximal direction may cause the plurality of splines 30 to flex radially outward and deploy the electrode array 16 as shown in FIG. 2B.

In use, the cardiac mapping catheter 10 may be inserted into a patient's vasculature with the electrode array 16 in the undeployed, radially retracted position shown in FIG. 2A and advanced to the interior of the patient's heart. Once within the heart, the electrode array 16 may be deployed by deployment control 26 as described above into the radially extended position shown in FIG. 2B to sense the cardiac signals within the heart. The sensed cardiac signals may be transmitted to the mapping data recording and analysis system by way of the set of electrical conductors extending through the lead body 14 from the electrode array 16 to handle 12, and electrical connection 18. Once the cardiac mapping is completed, the electrode array 16 may be undeployed into the radially retracted position and withdrawn from the patient.

As shown in FIGS. 2A and 2B, each of the electrodes 36 may be formed on the flexible polymer substrate 34. In some embodiments, the electrodes 36 are able to flex with deployment of the electrode array 16, while also maintaining low impedance and biocompatibility. In some embodiments, once the electrode array 16 is deployed, at least some of the electrodes 36 may be curved. The electrodes 36 are shown in FIGS. 2A and 2B as circular in shape. However, embodiments having other shapes, such as rectangular, oval, racetrack, or a combination of shapes are envisioned.

Figure 3:
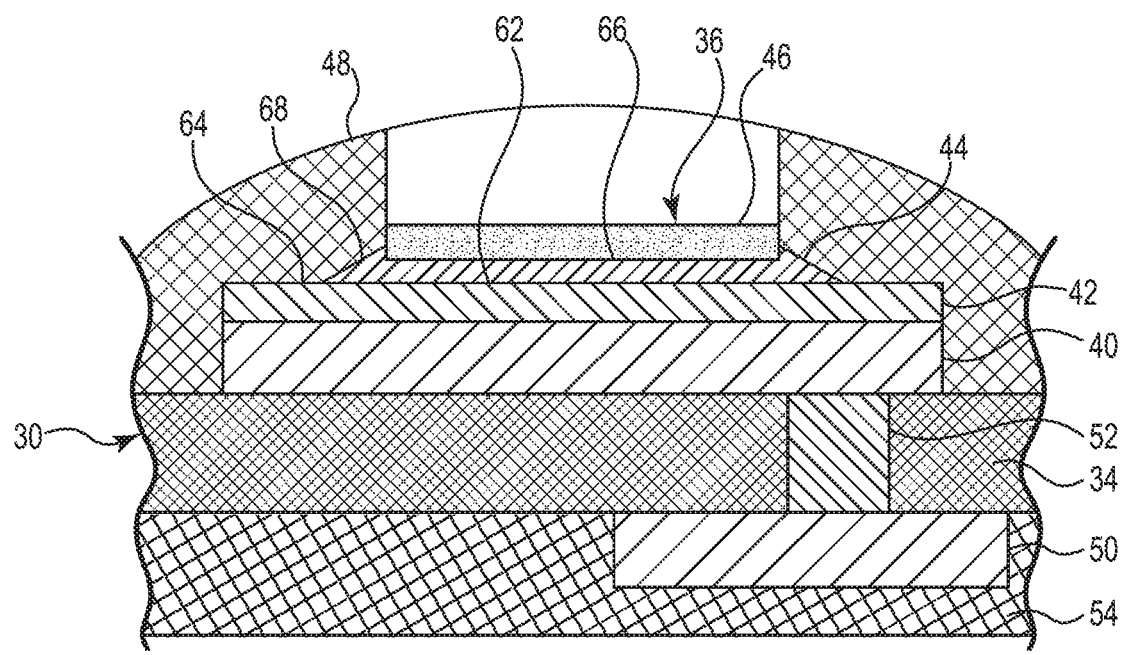
FIG. 3 is a schematic cross-sectional view of an electrode in accordance with embodiments of the present invention.

FIG. 3 illustrates details of the electrode 36 in accordance with embodiments of the present invention. For clarity, a single electrode 36 is illustrated in FIGS. 3-12. FIG. 3 is a schematic cross-sectional view of one of the splines 30 through one of the electrodes 36. As shown in FIG. 3, the electrode 36 may include a conductive layer 40, an intermediate metal layer 42, an iridium-containing layer 44, an iridium oxide layer 46, and an insulating polymer layer 48. The conductive layer 40 may be formed on a portion of the flexible polymer substrate 34. The intermediate metal layer 42 may be formed on at least a portion of the conductive layer 40. The iridium-containing layer 44 may be formed on a first portion 62 of the intermediate metal layer 42, and may not be formed on a second portion 64 of the intermediate metal layer 42. The iridium oxide layer may be formed on a first portion 66 of the iridium-containing layer 44, and may not be formed on a second portion 68 of the iridium-containing layer 44. The insulating polymer layer 48 may be formed on the second portion 64 of the intermediate metal layer 42, and the second portion 68 of the iridium-containing layer 44. The insulating polymer layer 48 may not be formed on the iridium-oxide layer 46.

In some embodiments, the conductive layer 40 may be made of a non-biocompatible material, such as copper or a copper alloy. The conductive layer 40 may have a suitable thickness. For example, the conductive layer 40 may have a thickness of as little as about 2 microns, about 4 microns, about 6 microns, or about 7 microns, or as great as about 9 microns, about 10 microns, about 12 microns, or about 14 microns, or have thickness within any range defined between any pair of the foregoing values. In exemplary embodiments, the conductive layer 40 may have a thickness from about 2 microns to about 14 microns, from about 4 microns to about 12 microns, from about 6 microns to about 10 microns, or from about 7 microns to about 9 microns. In some examples, the conductive layer 40 may have a thickness of about 8 microns.

In some embodiments, the intermediate metal layer 42 may be made of gold or a gold alloy and may have a suitable thickness. For example, in some embodiments, the intermediate metal layer 42 may have a thickness of as little as about 0.1 microns, about 0.5 microns, or about 1 micron, or as great as about 2 microns, about 3 microns, or about 4 microns, or have thickness within any range defined between any pair of the foregoing values. In exemplary embodiments, the intermediate metal layer 42 may have a thickness from about 0.1 microns to about 4 microns, from about 0.5 microns to about 3 microns, or from about 1 micron to about 2 microns. In some examples, the intermediate metal layer 42 may have a thickness of about 1.5 microns. The intermediate metal layer 42 may provide oxidation protection of the underlying conductive layer 40, and provide an additional barrier between the conductive layer and body tissues.

In some embodiments, the iridium-containing layer 44 may be formed primarily of iridium. For example, iridium may be present in the iridium-containing layer 44 in an amount as little as about 50 wt. %, about 60 wt. %, or about 70 wt. %, or as great as about 80 wt. %, about 90 wt. %, or about 100 wt. %, or may be present within any range defined between any pair of the foregoing values. In exemplary embodiments, iridium may be present in the iridium-containing layer 44 in an amount from about 50 wt. % to about 100 wt. %, from about 60 wt. % to about 90 wt. %, or from about 70 wt. % to about 80 wt. %. In some examples, iridium-containing layer 44 may include at least 99 wt. % iridium. In some embodiments, the iridium-containing layer 44 may be formed primarily of iridium and platinum may make up the balance. For example iridium may be present in the iridium-containing layer 44 in an amount as little as about 50 wt. %, about 60 wt. %, or about 70 wt. %, or as great as about 80 wt. %, about 90 wt. %, or about 99 wt. %, or may be present within any range defined between any pair of the foregoing values, and the balance platinum. In exemplary embodiments, iridium may be present in the iridium-containing layer 44 in an amount from about 50 wt. % to about 100 wt. %, from about 60 wt. % to about 90 wt. %, or from about 70 wt. % to about 80 wt. %, and the balance platinum.

In some embodiments, the insulating polymer layer 48 may be a biocompatible polymer, such as a biocompatible parylene polymer. In some embodiments, the parylene polymer may be one of poly(p-xylylene) also known as parylene N, poly(monochloro-p-xylylene) also known as parylene C, or poly(dichloro-p-xylylene) also known as parylene D. In exemplary embodiments, the parylene polymer may be poly(monochloro-p-xylylene).

As shown in FIG. 3, the spline 30 may further include an electrical trace 50, an electrical interconnect 52, and a backside insulating layer 54. The electrical trace 50 may be formed on a side of the flexible polymer substrate 34 opposite the conductive layer 40. The electrical trace 50 runs along a length of the spline 30 to one of the set of electrical conductors extending through the lead body 14 (FIG. 1). The electrical interconnect 52 extends through the flexible polymer substrate 34 from the electrical trace 50 to the conductive layer 40 to electrically connect the electrode 36 to the electrical trace 50. The backside insulating layer 54 covers the electrical trace 50 and at least a portion of the flexible polymer substrate 34 on the side of the flexible polymer substrate 34 opposite the conductive layer 40 to electrically isolate the electrical trace 50.

The flexible polymer substrate 34 may be made of a polyimide polymer. The electrical trace 50 and the electrical interconnect 52 may be made of copper or a copper alloy. The backside insulating layer 54 may also be made of a polyimide polymer and may itself be biocompatible, or may be covered with an additional biocompatible layer (not shown).

Figure 4:
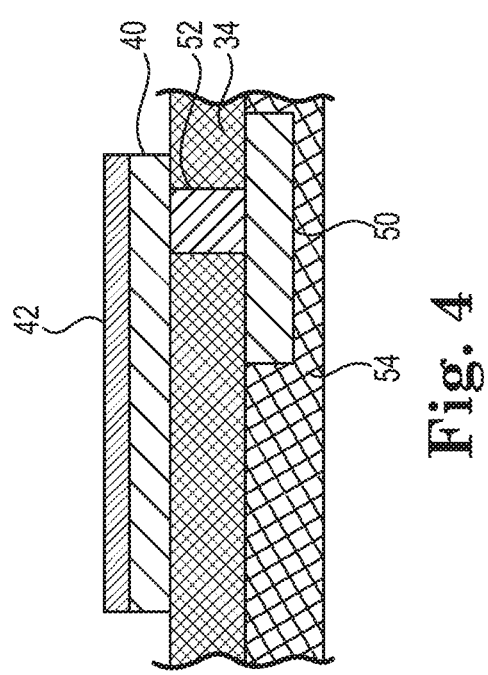

FIGS. 4-12 are schematic views illustrating a method for fabricating the electrode 36 shown in FIG. 3 in accordance with embodiments of the present invention. The method may begin as shown in FIG. 4 with the flexible polymer substrate 34, the conductive layer 40, the intermediate metal layer 42, the electrical trace 50, and the electrical interconnect 52 already made in the form of a flexible printed circuit (FPC). The conductive layer 40 and the intermediate metal layer 42 may already be patterned to form a basis of the electrode 36 as shown. The backside insulating layer 54 may be included in the FPC as shown, or may be attached by an adhesive in a separate step at any point in the fabrication process.

As shown in FIG. 5, a first mechanical mask 76 may be applied to the flexible polymer substrate 34. The first mechanical mask 76 includes a first opening 78 (one shown) for each of the electrodes 36. In some embodiments, the first opening 78 is smaller than the pattern of the intermediate metal layer 42 such that when the first mechanical mask 76 is applied to the intermediate metal layer 42, the edges of the intermediate metal layer 42 are not exposed. That is, the first mechanical mask 76 may be aligned to cover the edges of the intermediate metal layer 42 while at least a portion of the intermediate metal layer 42 may be exposed through the first opening 78.

As shown in FIG. 6, after the first mechanical mask 76 is applied, the iridium-containing layer 44 may be deposited on the portion of the surface of the intermediate metal layer 42 exposed by the first opening 78. Deposition of the iridium-containing layer 44 may be by any of a number of methods known in the art, for example, sputter deposition or evaporative deposition. Edges of the first mechanical mask 76 may not be perfectly square or in perfect contact with the intermediate metal layer 42 and some deposited material will deposit, or "bleed", under the edges of the first mechanical mask 76. As a result, a deposited area of the iridium-containing layer 44 may be larger than the first opening 78, but smaller than the area of the intermediate metal layer 42. In some embodiments, a layer 80 of the deposited iridium-containing metal may also be formed on the first mechanical mask 76 during deposition. After deposition of the iridium-containing layer 44, the first mechanical mask 76 may be removed as shown in FIG. 7. In this way, the first portion 62 of the intermediate metal layer 42, which is covered by the iridium-containing layer 44, and the second portion 64 of the intermediate metal layer 42, which is not covered by the iridium-containing layer 44, may be formed as shown in FIG. 7.

In some embodiments, the iridium-containing layer 44 as deposited may have a suitable thickness. For example, in some embodiments, the iridium-containing layer 44 may have a thickness of as little as about 0.1 microns, about 0.2 microns, or about 0.4 microns, or as great as about 0.6 microns, about 0.8 microns, or about 1 micron, or have a thickness within any range defined between any pair of the foregoing values. In exemplary embodiments, the iridium-containing layer 44 may have a thickness from about 0.1 microns to about 1 micron, from about 0.2 microns to about 0.8 microns, or from about 0.4 microns to about 0.6 microns. In some examples, the iridium-containing layer 44 may have a thickness of about 0.5 microns as deposited.

As shown in FIG. 8, after the formation of the iridium-containing layer 44, the insulating polymer layer 48 may be deposited on the flexible substrate 34, the conductive layer 40, the intermediate metal layer 42, and the iridium-containing layer 44. Deposition of the insulating polymer layer 48 may by, for example, dip coating, spray coating, or vapor deposition. In some embodiments, the insulating polymer layer 48 includes a parylene polymer and the parylene polymer may be deposited by vapor deposition. The vapor deposition of the parylene polymer may include sublimation of a parylene dimer, pyrolization of the parylene dimer to form a parylene monomer, and condensation of the parylene monomer onto the flexible substrate 34, the conductive layer 40, the intermediate metal layer 42, and the iridium-containing layer 44 to form the insulating polymer layer 48. In some embodiments, the parylene polymer may be poly(monochloro-p-xylylene) produced from a dichloro-[2,2]-paracyclophane dimer. In other embodiments, the parylene polymer may be poly(p-xylylene) produced from a [2,2]-paracyclophane dimer. In some embodiments, the parylene polymer may poly(dichloro-p-xylylene) produced from a tetrachloro-[2,2]-paracyclophane dimer.

Figure 9:
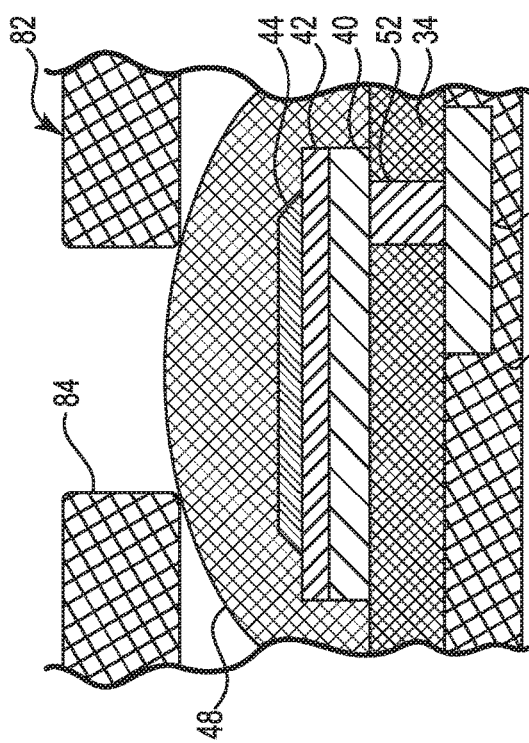
Figure 10:
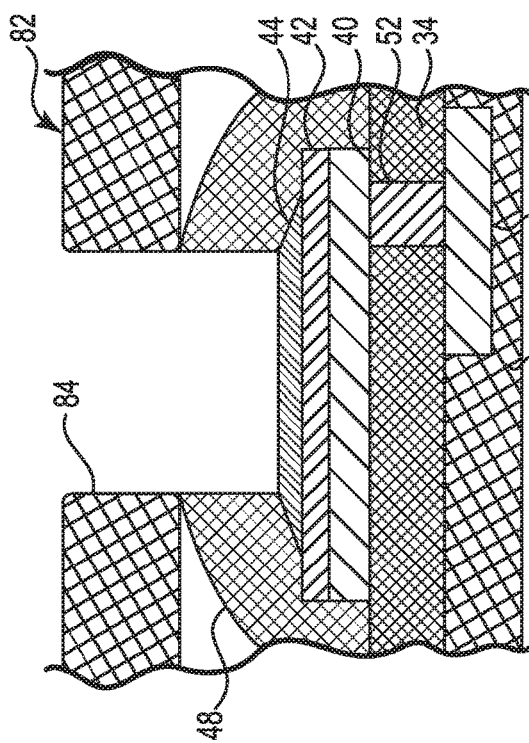
Figure 11:
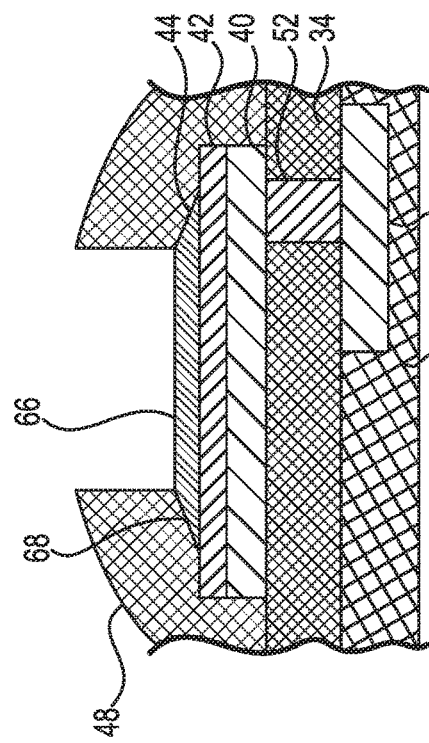

Following deposition of the insulating polymer layer 48, the insulating polymer layer 48 over a portion of the iridium-containing layer 44 may be removed. In some embodiments, removing the insulating polymer layer 48 from the portion of the iridium-containing layer 44 may be as shown in FIGS. 9-11. As shown in FIG. 9, a second mechanical mask 82 may be applied to the flexible polymer substrate 34. The second mechanical mask 82 includes a second opening 84 (one shown) for each of the electrodes 36. In some embodiments, the second opening 84 is smaller than the first opening 78 of the first mechanical mask 76. In other embodiments, the second opening 84 is about the same size as the first opening 78. In still other embodiments, the second mechanical mask 82 and the first mechanical mask 76 may be the same mask. In any of the aforementioned embodiments, when the second mechanical mask 82 is applied to the iridium-containing layer 44, the edges of the iridium-containing layer 44 are not exposed through the second opening 84. That is, the second mechanical mask 82 may be aligned to cover the edges of the iridium-containing layer 44 while at least a portion of the iridium-containing layer 44 may be exposed through the second opening 84.

As shown in FIG. 10, after the second mechanical mask 82 is applied, the insulating polymer layer 48 exposed by the second opening 84 may be removed by laser ablation, as is known in the art. The second mechanical mask 82 protects the insulating polymer later 48 formed on the edge of the iridium-containing layer 44, as well as on the flexible polymer substrate 34, the second portion 60 of the conductive layer 40, and the second portion 64 of the intermediate metal layer 42. After laser ablation of the insulating polymer layer 48, the second mechanical mask 82 may be removed as shown in FIG. 11. In this way, the first portion 66, which is not covered by the insulating polymer layer 48, and the second portion 68, which is covered by the insulating polymer later 48, of the iridium-containing layer 44 may be formed as shown in FIG. 11. Alternatively, in some embodiments, a spot size of the laser used for laser ablation may be small enough compared to the size of the first portion 66, and the accuracy with which the laser spot may be positioned may be great enough, that the insulating polymer layer 48 may be removed without the need for the protection of the second mechanical mask 82.

Figure 12:
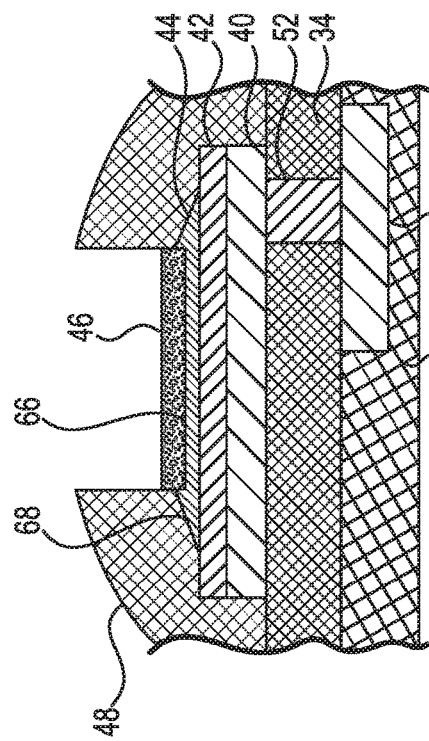

As shown in FIG. 12, after formation of the insulating polymer layer 48, the iridium-containing layer 44 may be activated by forming the iridium oxide layer 46 on the first portion 66 of the iridium-containing layer 44. The activation may reduce the electrical impedance of the electrode 36 by as much as three orders of magnitude compare to the electrode 36 without the iridium oxide layer 46.

In some embodiments, the iridium oxide layer 46 may be formed by electrochemically oxidizing the first portion 66 of the iridium-containing layer 44. In some embodiments, the flexible polymer substrate 34 may be immersed in an electrolytic solution such that the first portion 66 of the iridium-containing layer 44 may be exposed to an electrolytic solution. Examples of the electrolytic solution may include a saline solution such as phosphate buffered saline solution. A cathode may also be positioned within the electrolytic solution and a voltage may be applied between the cathode and the electrode 36 to pass an electrical current between the cathode and the electrode 36. Oxygen may be released from the electrolytic solution when the voltage is applied. The released oxygen reacts with the iridium of the iridium-containing layer 44 to form the iridium oxide layer 46. In some embodiments, the voltage may be cycled between positive and negative voltages until a desired thickness of iridium oxide is formed. Once the desired thickness of iridium oxide is formed, the flexible polymer substrate 34 may be removed from the electrolytic solution. Forming the iridium oxide layer 46 in this way may produce improved adhesion of the iridium oxide layer 46 compared to, for example, sputter depositing a layer of iridium oxide directly. In addition, the iridium oxide layer 46 may provide improved electrical performance by reducing impedance of the electrode 36 by at least 25% compared to sputter depositing a layer of iridium oxide directly.

As shown in FIG. 12, the thickness of the iridium-containing layer 44 at the first portion 66 may decrease from its as-deposited thickness as iridium from the iridium-containing layer 44 reacts to form the iridium oxide layer 46. In some embodiments, following activation, the iridium-containing layer 44 at the first portion 66 may have a thickness as little as about 10%, about 20%, about 30%, or about 40%, or as much as about 60%, about 70%, about 80%, or about 90% of the as-deposited thickness, or have thickness within any range defined between any pair of the foregoing values. In exemplary embodiments, following activation, the iridium-containing layer 44 may have a thickness from about 10% to about 90%, from about 20% to about 80%, from about 30% to about 70%, or from about 40% to about 60% of the as-deposited thickness. In some examples, iridium-containing layer 44 may have a thickness following activation that is about 50% of the as-deposited thickness.

The iridium-containing layer 44 may have a high melting point, such as in excess of 2000° C. The iridium-containing layer 44 may also have a partially reflective surface finish that reflects at least a portion of the laser energy from the surface during a laser ablation process. Thus, the iridium-containing layer 44 may be able resist laser damage while the insulating polymer layer 48 exposed by the second opening 84 is removed. This resistance to damage may allow for a more thorough removal of the insulating polymer layer 48 by a lengthier laser ablation process to produce a cleaner surface on the first portion 66 of the iridium-containing layer 44. The cleaner surface on the first portion 66 may allow the iridium oxide layer 46 to form more evenly over the first portion 66 of the iridium-containing layer 44 leading to improved impedance. The cleaner surface may also lead to improved adhesion of the iridium oxide layer 46 to the iridium-containing layer 44, which may enable electrodes 36 to be able to flex with deployment of the electrode array 16, while also maintaining low impedance and biocompatibility.

In the embodiments described above, each of the conductive layer 40, the intermediate metal layer 42, the iridium-containing layer 44, and the iridium oxide layer 46 is formed only on one other material which may lead to overall improved layer-to-layer adhesion by optimizing the deposition process for deposition on a single material. In addition, the electrode 36 may be biocompatible by having only the biocompatible materials exposed, such the insulating polymer layer 48 and the iridium oxide layer 46, and by not having any non-biocompatible materials exposed, such as the conductive layer 40.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A method for making an electrode for cardiac signal sensing, the electrode formed on a flexible polymer substrate having a conductive layer and an intermediate metal layer disposed on the conductive layer, the method comprising:
   depositing an iridium-containing layer onto a portion of the intermediate metal layer, the iridium-containing layer including at least 50 wt. % iridium;
   depositing an insulating polymer layer on the flexible polymer substrate, the conductive layer, the intermediate layer, and the iridium-containing layer;
   removing the insulating polymer layer from a portion of the iridium-containing layer to form an exposed surface; and
   electrochemically oxidizing at least a portion of the iridium-containing layer at the exposed surface to form an iridium oxide layer on the iridium-containing layer.

2. The method of claim 1, wherein removing the insulating polymer layer includes laser ablating the insulating polymer layer from the portion of the iridium-containing layer.

3. The method of claim 1, wherein depositing the insulating polymer layer includes depositing a parylene polymer by vapor deposition.

4. The method of claim 3 wherein the parylene polymer is poly(monochloro-p-xylylene).

5. The method of claim 1, wherein the intermediate metal layer includes gold.

6. The method of claim 1, wherein depositing the iridium-containing layer includes:
   applying a first mechanical mask to the substrate, the first mechanical mask including a first opening aligned with the intermediate metal layer to define the portion of the intermediate metal layer;
   depositing the iridium-containing layer by sputter deposition; and
   removing the first mechanical mask.

7. The method of claim 6, wherein removing the insulating polymer layer includes:
   applying a second mechanical mask to the substrate, the second mechanical mask including a second opening aligned with the portion of the iridium-containing layer, wherein the second opening is smaller than the first opening;
   laser ablating the insulating polymer layer from the portion of the iridium-containing layer; and
   removing the second mechanical mask.

8. The method of claim 6, wherein removing the insulating polymer layer includes:
   applying a second mechanical mask to the substrate, the second mechanical mask including a second opening aligned with the portion of the iridium-containing layer, wherein the second opening is the same size as the first opening;
   laser ablating the insulating polymer layer from the portion of the iridium-containing layer; and
   removing the second mechanical mask.

9. The method of claim 1, wherein electrochemically oxidizing includes:
   immersing the substrate in an electrolytic solution;
   cycling the iridium-containing layer between positive and negative voltages until a desired thickness of iridium oxide is formed on the surface of the portion of iridium-containing layer; and
   removing the substrate from the electrolytic solution.

* * * * *